United States Patent

Smith

[11] 4,340,042
[45] Jul. 20, 1982

[54] INFLATABLE SPLINT
[75] Inventor: Dennis M. Smith, South Bend, Ind.
[73] Assignee: B.A.G., Inc., South Bend, Ind.
[21] Appl. No.: 176,989
[22] Filed: Aug. 11, 1980
[51] Int. Cl.³ .................. A61B 17/18; A61F 5/04
[52] U.S. Cl. ................................ 128/87 R; 128/90; 128/DIG. 20
[58] Field of Search ............... 128/87 R, 89 R, 90, 128/DIG. 20, 118; 9/14, 301, 307, 310 F, 311, 316, 329, 336, 340, 344, 345

[56] References Cited
U.S. PATENT DOCUMENTS

| | | | |
|---|---|---|---|
| 1,127,930 | 2/1915 | Smack | 9/345 |
| 1,766,300 | 6/1930 | Meredith | 9/336 |
| 2,312,976 | 3/1943 | Pels | 9/301 |
| 2,950,489 | 8/1960 | Pattison | 9/340 |
| 3,242,923 | 3/1966 | Jacoby, Sr. | 128/DIG. 20 |
| 3,581,740 | 6/1971 | Sherbourne | 128/DIG. 20 |
| 4,135,503 | 1/1979 | Romano | 128/118 |
| 4,182,320 | 1/1980 | Sweeney | 128/DIG. 20 |

Primary Examiner—Kyle L. Howell
Assistant Examiner—C. W. Shedd
Attorney, Agent, or Firm—Oltsch, Knoblock & Hall

[57] ABSTRACT

An inflatable bag splint with straps which inhibits the bending of a joint. The bag is airtight with an inlet valve and the straps are situated so as to be placed about an arm or leg to prevent movement thereof.

2 Claims, 4 Drawing Figures

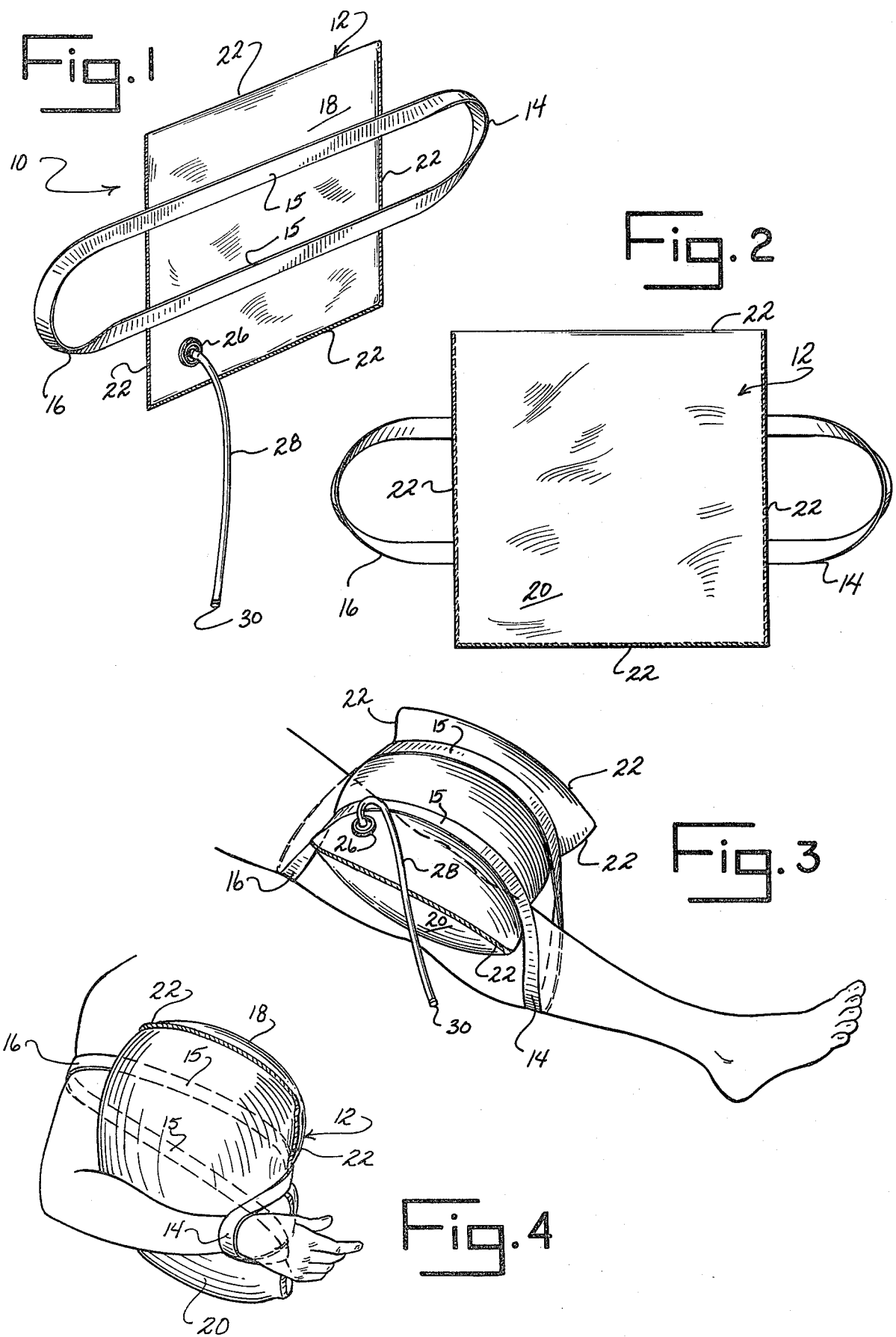

INFLATABLE SPLINT

SUMMARY OF THE INVENTION

This invention relates to an inflatable splint.

It oftentimes becomes necessary to immobilize a limb due to injury when medical assistance is not readily available. In these instances, it is not always possible, and may be impractical, to carry a portable splint while hiking, or engaging in other sports. The present invention serves to solve this problem. The inflatable splint of this invention is small enough so that it requires very little space in packing and allows the user to be prepared for an emergency.

The splint is made of an inflatable body with looped straps extending from it. The injured limb is inserted through the straps and the body of the splint is inflated. The inflation of the body exerts pressure on the straps about the limb, and thereby prevents movement of the limb. When not being used as a splint, the body may be used as a cushion for sitting and may hold drinking liquids.

Accordingly, it is the object of the invention to provide a means of immobilizing a limb.

Another object of the invention is to provide a portable inflatable splint.

Still another object of the invention is to provide a splint which is easily packed and carried.

Other objects will become obvious upon a further reading of the following description.

BRIEF DESCRIPTION OF THE DRAWINGS

FIG. 1 is a perspective view of the front of the splint.

FIG. 2 is a rear view of the splint.

FIG. 3 is a perspective view of the splint showing it in use on a leg.

FIG. 4 is a perspective view of the splint showing it in use in an arm.

DESCRIPTION OF THE PREFERRED EMBODIMENT

The preferred embodiment illustrated is not intended to be exhaustive or to limit the invention to the precise form disclosed. It is chosen and described in order to best explain the principles of the invention and its application and practical use to thereby enable others skilled in the art to best utilize the invention.

Referring to FIGS. 1 and 2, splint 10 includes a body 12 and straps 14, 16. Body 12 is composed of an air and liquidtight material such as plastic or rubber sheeting and may be covered with a durable cover composed of a cloth or nylon material. Body 12 has a front surface 18 and a rear surface 20 enclosed by a peripheral edge 22. A continuous strap 15 is connected to front surface 18 of body 12 and includes loop parts 14, 16 which project from opposite sides of body peripheral edge 22. Body 12 has inlet valve 26 formed therein. Valve 26 has nozzle 28 extending from it and the nozzle is plugged with stopper 30.

To utilize splint 10, the injured limb such as leg 32 is inserted through strap loop 14 and then inserted through strap loop 16 with rear body surface 20 positioned against the limb as seen in FIG. 3. To prevent a limb from extending, splint 10 is positioned as seen in FIG. 4. When body 12 is properly positioned against the limb and strap loops 16 and 14 located about the limb, the body is inflated through nozzle 28 and stopper 30 replaced.

To immobilize a knee, the foot of the user is placed through strap loop 14 and then through strap loop 16 with the strap loop passing behind the leg. The body 12 of splint 10 is then placed atop the knee and inflated. This prevents bending of the knee. If the leg is desired to be kept in a bent position, strap loop passes about the front of the thigh and loop 16 passes around the front of the shin, and the body 12 is then inflated. Splint 10 is also capable of being used on other moveable joints, such as ankles and wrists.

It is noted that splint 10 is not limited to use as an immobilizer. With proper insulation, body 12 can be filled with a hot or cold liquid to provide a hot pack or cold pack. Splint 10 can also be utilized as an inflatable pillow or pad. To carry splint 10, the user passes his arms through strap loops 14 and 16 and wears the splint as a backpack.

It is understood that the invention is not to be limited to the preceding description, but may be amended within the scope of the appended claims.

I claim:

1. An inflatable splint comprising a body and a strap; said strap including first and second interconnected strap loop parts; said body being of single piece form and composed of a fluidtight expandable material and including valve means for filling and emptying the body of a fluid; said body being defined by a front surface, a rear surface, and a peripheral edge having opposed portions; said first strap loop part being secured to said body front surface adjacent a portion of said peripheral edge and extending from said body; said second strap loop part being secured to said body front surface adjacent an opposed portion of said peripheral edge and extending from said body oppositely of said first strap loop part; said strap extending at two-spaced locations across said body front surface between said strap loop parts to form a resistance member when said body is inflated.

2. The splint of claim 1 wherein said body includes an insulative material for maintaining the temperature of a liquid within said body.

* * * * *